US008623022B2

(12) United States Patent
Forton et al.

(10) Patent No.: US 8,623,022 B2
(45) Date of Patent: Jan. 7, 2014

(54) SURGICAL INSTRUMENT SUPPORT SYSTEM AND METHOD (75) Inventors: Charles R. Forton, Leander, TX (US); Larry T. Khoo, Studio City, CA (US); Peter Thomas Miller, Austin, TX (US)

(73) Assignee: Zimmer Spine, Inc., Minneapolis, MN (US)

(*) Notice: Subject to any disclaimer, the term of this patent is extended or adjusted under 35 U.S.C. 154(b) by 481 days.

(21) Appl. No.: 12/885,673

(22) Filed: Sep. 20, 2010

(65) Prior Publication Data

US 2012/0071885 A1 Mar. 22, 2012

(51) Int. Cl.
- *A61F 2/46* (2006.01)
- *A61F 2/00* (2006.01)
- *A61B 17/58* (2006.01)
- *A61B 17/60* (2006.01)

(52) U.S. Cl.
USPC ........................................ 606/86 R; 606/104

(58) Field of Classification Search
USPC .................... 606/86 A, 104, 914, 916, 86 R
See application file for complete search history.

(56) References Cited

U.S. PATENT DOCUMENTS

| 4,505,268 | A | 3/1985 | Sgandura |
| 4,823,781 | A | 4/1989 | Buchanan |
| 7,060,066 | B2 | 6/2006 | Zhao et al. |
| 7,250,052 | B2 | 7/2007 | Landry et al. |
| 2004/0230191 | A1* | 11/2004 | Frey et al. .................. 606/57 |
| 2005/0070917 | A1 | 3/2005 | Justis |
| 2006/0036255 | A1 | 2/2006 | Pond et al. |
| 2006/0095035 | A1 | 5/2006 | Jones et al. |
| 2006/0122597 | A1 | 6/2006 | Jones et al. |
| 2006/0167454 | A1 | 7/2006 | Ludwig et al. |
| 2006/0217735 | A1 | 9/2006 | MacDonald et al. |
| 2006/0247630 | A1 | 11/2006 | Iott et al. |
| 2006/0264934 | A1 | 11/2006 | Fallin |
| 2007/0083210 | A1 | 4/2007 | Hestad et al. |
| 2007/0112351 | A1 | 5/2007 | Assell et al. |
| 2007/0162010 | A1 | 7/2007 | Chao et al. |
| 2007/0213714 | A1 | 9/2007 | Justis |
| 2008/0015582 | A1 | 1/2008 | DiPoto et al. |
| 2008/0077139 | A1 | 3/2008 | Landry et al. |
| 2008/0077155 | A1 | 3/2008 | Diederich et al. |
| 2008/0082103 | A1 | 4/2008 | Hutton et al. |
| 2008/0119852 | A1 | 5/2008 | Dalton et al. |

(Continued)

FOREIGN PATENT DOCUMENTS

WO    WO2009/158707    12/2009

OTHER PUBLICATIONS

International Search Report and Written Opinion issued for PCT Application No. PCT/US2011/049196, mailed Nov. 15, 2011, 13 pages.

*Primary Examiner* — Sameh Boles
(74) *Attorney, Agent, or Firm* — Seager, Tufte & Wickhem, LLC (57) ABSTRACT

Embodiments include a system for manipulating a portion of the spine. A support body provides support for extender sleeves that are coupled to bone screws implanted in bone. The extender sleeves are coupled to the support body in a manner that allows translation and rotation of the extender sleeves relative to the support body. Movement and rotation of the extender sleeves in selected directions can be allowed while movement and rotation in other directions can be inhibited. The extender sleeves can be manipulated to move the bone.

21 Claims, 4 Drawing Sheets

(56) References Cited

U.S. PATENT DOCUMENTS

| | | |
|---|---|---|
| 2008/0154280 A1 | 6/2008 | Schumacher et al. |
| 2008/0172062 A1 | 7/2008 | Donahue et al. |
| 2008/0177269 A1 | 7/2008 | Seelig |
| 2009/0228053 A1 | 9/2009 | Kolb et al. |
| 2010/0036443 A1 | 2/2010 | Hutton et al. |

* cited by examiner

SURGICAL INSTRUMENT SUPPORT SYSTEM AND METHOD

TECHNICAL FIELD

The present disclosure generally relates to surgical tools and in particular to an external support with multiple components that may be controlled individually to manipulate the spine during spinal surgery.

BACKGROUND

The human spine consists of segments known as vertebrae linked by intervertebral disks and held together by ligaments. There are 24 movable vertebrae—7 cervical (neck) vertebrae, 12 thoracic (chest) vertebrae, and 5 lumbar (back) vertebrae. Each vertebra has a somewhat cylindrical bony body (centrum), a number of winglike projections (processes), and a bony arch. The arches are positioned so that the space they enclose forms the vertebral canal. The vertebral canal houses and protects the spinal cord, and within it the spinal fluid circulates. Ligaments and muscles are attached to various projections of the vertebrae. The bodies of the vertebrae form the supporting column of the skeleton. Fused vertebra make up the sacrum and coccyx, the very bottom of the vertebral column.

The spine is subject to abnormal curvature, injury, infections, tumor formation, arthritic disorders, and puncture or slippage of the cartilage disks. Modern spine surgery often involves the use of spinal stabilization/fixation procedures such as a vertebral body fusion procedure to correct or treat various acute or chronic spine disorders and/or to support the spine. In conjunction with these procedures, some spinal implants may be utilized to help stabilize the spine, correct deformities of the spine such as spondylolisthesis or pseudoarthrosis, facilitate fusion, or treat spinal fractures. Some spinal fixation systems may provide fused and/or rigid support for the affected regions of the spine. For example, a spinal fixation system may include a corrective spinal implant that is attached to selected vertebrae of the spine by screws, hooks, and clamps. The corrective spinal implant may include spinal rods or plates that are generally parallel to the patient's back. The corrective spinal implant may also include transverse connecting rods that extend between neighboring spinal rods. Spinal fixation systems can be used to correct problems in the cervical, thoracic, and lumbar portions of the spine, and are often installed posterior to the spine on opposite sides of the spinous process and adjacent to the transverse process. Spinal fixation systems when implanted inhibit movement in the affected regions in virtually all directions.

More recently, so called "dynamic" systems have been introduced. Dynamic spinal stabilization systems can better match a patient's anatomy than some spinal stabilization systems used to provide static support. When implanted in a patient, a dynamic spinal stabilization system can allow at least some movement (e.g., flexion, extension, lateral bending, or torsional rotation) of the affected regions of the spine in at least some of the directions, giving the patient a greater range of motion. Dynamic stabilization systems can be used in scenarios in which vertebral body fusion is not desired, in which vertebral body (re)alignment is desired, and in which it is desired to support or strengthen degraded, diseased, damaged, or otherwise weakened portions of the spine.

Often, spinal stabilization systems include rods which can bear a portion of the forces that would otherwise be transmitted along the spine. These rods may be implanted in pairs or in other numbers along portions of the spine of interest. Some spinal stabilization systems may support a portion of the spine including only two vertebrae (and associated anatomical structures) while some spinal stabilization systems support portions of the spine extending beyond two vertebrae. Spinal stabilizations systems can be used to support various portions of the spine, including the lumbar portion of the spine and the thoracic portion of the spine. Regardless of the number of rods implanted, or the portion of the spine in which they may be implanted, the rods can be attached to one or more vertebrae of the spine to provide support and stabilize, align, or otherwise treat the region of the spine of interest. Surgical personnel may use one or more anchor systems to attach the rods to one or more vertebrae. One such anchor system includes pedicle screws constructs which define slots, keyways, grooves, apertures, or other features for accepting and retaining stabilization rods which may be static, dynamic, or a combination of both. In many pedicle screw constructs, pedicle screws are placed in vertebrae selected by surgical personnel.

Severe conditions such as scoliosis, burst fractures and other deformities often require manipulation of the vertebrae. In some surgical systems, translation (compression or distraction) of vertebral bodies is possible only if the rod is already placed and one of the vertebral bodies has been provisionally locked to the rod. Once the manipulation has been completed, the second vertebral body must be locked to the rod or movement will not be fixed. If a second type of manipulation (i.e., angular rotation) is required, the implants must be unlocked to allow the manipulation, which can result in the original movement being undone.

SUMMARY

Embodiments of a surgical instrument support system described herein do not require a spinal stabilization rod to be installed until after the movement has been completed. Advantageously, consecutive movements may be performed and held in place by various components, enabling percutaneous and minimally invasive surgery techniques to be used to correct increasingly complex deformities or treat trauma.

According to one embodiment, a system for positioning components in a surgical procedure is provided. The system can include a support body to support extender sleeves that are used to manipulate the vertebrae. A support body collar is mounted to the support body and can translate along the support body. A linkage is coupled to the support body collar and can translate perpendicular (or other selected angle) to the support body collar. A sleeve collar is connected to the linkage by a connection that allows polyaxial rotation of the sleeve collar. The sleeve collar is sized to receive an extender sleeve and allow translation of the extender sleeve in the sleeve collar. Through movement of the various components, the sleeve can be placed in a desired location and orientation relative to a patient's body. Locking mechanisms can be used to selectively inhibit motion of the support body collar relative to the support body, the linkage relative to the support body collar, the sleeve collar relative to the linkage and the sleeve relative to the sleeve collar. For various steps in a surgical procedure, the surgeon can configure the system to allow only motion in selected directions while preventing undesired motion. Motion of an extender sleeve can be allowed or inhibited for each procedural step as needed or desired.

According to one embodiment, a method for treating spinal injuries can comprise providing a rigid support body coupled to a set of extender sleeves. The support body provides support for the extender sleeves outside of a human body and the extender sleeves can translate and rotate relative the support body. The method can further comprise determining a desired longitudinal position and orientation of each of the set of extender sleeves and locking each of the set of extender sleeves in the desired longitudinal position and orientation. The method can further comprise advancing a set of bone anchors into vertebrae using the extender sleeves. The method can further comprise allowing selected translation and rotation of each extender sleeve relative to the support body while continuing to inhibit other translation and rotation relative to the support body. The extender sleeves can be manipulated to move selected vertebrae. The position and orientation of each of the set of extender sleeves can be locked when the selected vertebrae are in desired positions Embodiments of a surgical instrument support system may be beneficial in the treatment or correction of a spine having a deformity. The surgical instrument support system may be attached to the affected spine and one or more vertebrae may be moved individually or as a unit to correct the curvature of the spine, ensure proper positioning of vertebrae, or perform other translational or rotational adjustments until the spine has the correct curvature and alignment.

Other objects and advantages of the embodiments disclosed herein will be better appreciated and understood when considered in conjunction with the following description and the accompanying drawings.

BRIEF DESCRIPTION OF THE DRAWINGS

A more complete understanding of the present disclosure and the advantages thereof may be acquired by referring to the following description, taken in conjunction with the accompanying drawings in which like reference numbers indicate like features and wherein.

DETAILED DESCRIPTION

As used herein, the terms "comprises," "comprising," "includes," "including," "has," "having" or any other variation thereof, are intended to cover a non-exclusive inclusion. For example, a process, product, article, or apparatus that comprises a list of elements is not necessarily limited to only those elements but may include other elements not expressly listed or inherent to such process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance," "e.g.," "in one embodiment," and the like.

A spinal stabilization system may be installed in a patient to stabilize a portion of a spine. Spinal stabilization systems are often installed in patients having degenerative disc disease, spinal stenosis, spondylolisthesis, pseudoarthrosis, and/or spinal deformities; patients having fracture or other vertebral trauma; and patients having undergone tumor resection. A spinal stabilization system may be installed using a minimally invasive procedure. An instrumentation set may include instruments and spinal stabilization system components for forming a spinal stabilization system in a patient.

A minimally invasive procedure may be used to limit an amount of trauma to soft tissue surrounding vertebrae that are to be stabilized. In some embodiments, the natural flexibility of skin and soft tissue may be used to limit the length and/or depth of an incision or incisions needed during the stabilization procedure. Minimally invasive procedures may provide limited direct visibility in vivo. Forming a spinal stabilization system using a minimally invasive procedure may include using tools to position system components in the body.

Embodiments described in this disclosure provide systems and methods for using a surgical instrument support to position tools during a spinal stabilization procedure. In particular, embodiments of a surgical instrument support system can be positioned over a patient to hold tools in a manner that allows the tools to be used to correct the alignment of a deformed spinal column, repair damaged portions of the spine, and stabilize the spine. The surgical instrument support can be rigidly attached to a table or other surgical platform and tools may be coupled to the body of the surgical instrument support. The tools can be coupled to the support body in manner that allows a surgeon to move the tools along the surgical instrument support and lock the tools in desired positions and orientations. In some cases, the surgeon can lock the tools with respect to motion in one or more directions while allowing the tool to move in other directions during surgery. The surgeon can manipulate the supported tools to reposition the vertebrae during procedures to treat deformities or trauma.

Figure 1:
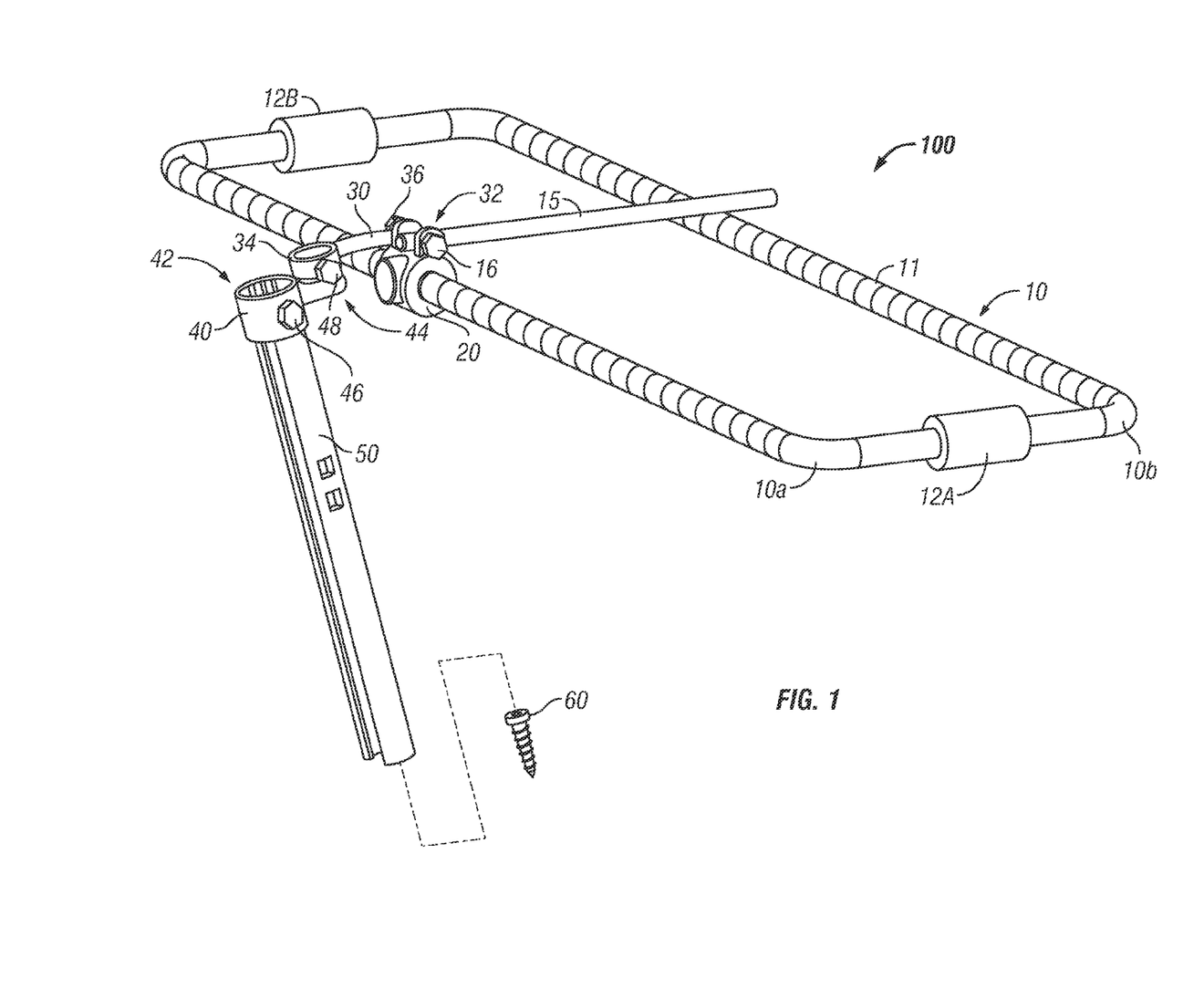
FIG. 1 depicts a perspective view of one embodiment of a surgical instrument support for positioning relative to a portion of the spine.

FIG. 1 depicts a diagrammatic representation of system 100 usable to adjust the alignment of a spinal column, provide access to damaged or degenerative vertebrae, discs or other spine components and stabilize the spine. System 100 may include a support body 10, crossbar 15, support body collar 20, linkage 30 and sleeve collar 40. Support body 10 can be used to support one or more extender sleeves 50. An extender sleeve 50 is a sleeve that can detachably couple to a bone anchor 60 and provide a working passage from the surface of the patient's body to bone anchor 60 so that tools, closure tops or other components can be guided to the bone anchor.

Example extender sleeves include, but are not limited to, extender sleeves for the PATHFINDER Pedicle Screw System by ZIMMER SPINE of Minneapolis, Minn.

Support body 10 can be formed as a single piece, or can be formed having members 10a and 10b joined by connectors 12a and 12b. In one embodiment, members 10a and 10b can be coupled together in a manner that allows the width of support body 10 to be adjusted. By way of example, but not limitation, members 10a and 10b can slide relative to each other. Support body 10 may include markings 11, which may be useful for a surgeon to determine a characteristic of the spine, such as the separation between adjacent vertebrae during a distraction procedure. Support body 10 may have a curvature generally parallel to the curvature of a spine or a desired curvature of the spine, can be straight or have other desired shape. Support body 10 may be sized for positioning over a single vertebra or a small incision such as found in minimally invasive surgery (MIS), or may be sized for procedures involving multiple MIS incisions or vertebrae.

System 100 can include body collars 20 for translation of components relative to support body 10. Support body collar 20 can be translated along support body 10 parallel to the longitudinal axis of the spine so that sleeve 50 can be placed at the appropriate vertebra. In one embodiment, support body collar 20 can also be rotated relative to support body 10. According to one embodiment, support body 10 may have a generally circular outer cross-sectional profile and support body collars 20 may have a generally circular inner cross-sectional profile to allow rotation of support body collars 20 relative to support body 10 about an axis. Assuming support body 10 is oriented so that the long portions of members 10a and 10b are parallel to the longitudinal axis of the spine, the axis of rotation of collars 20 will also be parallel to the longitudinal axis of the spine. In another embodiment, the outer surface of support body 10 and inner surface of support body collars 20 may have complementary angular cross-sections to prevent rotation of support body collars 20.

Support body collars 20 may include a support body collar locking mechanism to inhibit translational or rotational movement of support body collar 20 relative to support instrument support 10. A locking mechanism on support body collar 20 may directly engage support instrument support 10 to inhibit movement. For example, the locking mechanism can include a ball or pin in collar 20 that rests in complementary holes/detents in support body 10. In another embodiment, the locking mechanism can include a set screw that advances in support body collar 20 to bias support body 10 against support body collar 20. According to one embodiment, for example, a surgeon can turn knob 46 to easily advance the set screw. In other embodiments a squeeze connection other friction fit can be used. In yet other embodiments, other mechanisms known in the art can act to prevent translation and/or rotation of collar 20 relative to support body 10. A single locking mechanism or separate locking mechanisms can be used to prevent translation and rotation.

System 100 may further include crossbar 15 having a length for spanning the width of support instrument support 10. According to one embodiment, crossbar 15 can translate relative to support body collar 20. In some embodiments, a mechanism used to allow or inhibit movement of crossbar 15 relative to support body collar 20 includes crossbar set screw 16. Advancement of crossbar set screw 16 in support body collar 20 may bias support body collar 20 or support instrument support 10 against crossbar 15 to generate a friction force large enough to inhibit movement of crossbar 15 relative to support body collar 20. Other embodiments can use other locking mechanism to inhibit movement of crossbar 15 relative to support body collar 20. According to one embodiment, crossbar 15 can be coupled to support body collar 20 at each end to keep support body collars 20 on members 10a and 10b laterally aligned. Crossbar 15 may also be used to mount additional surgical tools.

System 100 may further include linkage 30 slidably and rotatably connected to support body collar 20. According to one embodiment, support body collar 20 can define a passage into which linkage 30 fits. Linkage 30 can translate laterally in the passage to adjust the distance of sleeve 50 from support instrument support 10. Linkage 30 may be generally straight or may have a bend or curve. In addition to translating, linkage 30, according to one embodiment, can rotate about an axis perpendicular to the longitudinal axis of the spine. This rotation can orient the sleeve at an angle relative to the anterior-posterior axis of the body.

A linkage locking mechanism can used to selectively inhibit translation and/or rotation of linkage 30. One example of a mechanism used to allow or inhibit movement of linkage 30 relative to support body collar 20 is linkage set screw 36. By advancing linkage set screw 36 into threads on support body collar 20, linkage set screw 36 may contact linkage 30. Additional advancement of linkage set screw 36 in support body collar 20 may bias linkage 30 against support body collar 20 to generate a friction force large enough to inhibit movement of linkage 30 relative to support body collar 20. Other examples of locking mechanisms can include a ball or pin that rests in a complementary hole/detent in linkage 30, a squeeze connection or other friction fit or other mechanism known in the art that can act to prevent translation and/or rotation of linkage 30. A single locking mechanism or separate locking mechanisms can be used to prevent translation and rotation.

An end of sleeve collar 44 can be coupled to linkage 30 at connection 34 in a manner that allows rotational movement between sleeve collar 40 and linkage 30. In some embodiments, connection 34 between sleeve collar 40 and linkage 30 may provide polyaxial movement to allow the angle of sleeve 50 relative to anteriorposterior axis of the patient to be adjusted. One non-limiting example of such a connection is a ball and socket type joint. Second end 44 of sleeve collar 40 and second end 34 of linkage 30 may be locked using a sleeve collar locking mechanism to inhibit movement of sleeve collar 40 relative to linkage 30. According to one embodiment, a set screw, indent/detent, a squeeze connection or other friction fit or other mechanism known in the art can be used to inhibit relative movement of sleeve collar 40 and linkage 30. For example, set screw 46 can be advanced through the side of connection 46 to bias a ball in a ball and socket joint against the surface of the socket, thereby inhibiting movement of sleeve collar 44 relative to linkage 30.

Sleeve collar 40 can couple to extender sleeve 50. Sleeve collar 40 can have an open passage 42 with an inner cross-sectional profile to allow sleeve 50 to translate in sleeve collar 40. Passage 42 can also be shaped so that sleeve 50 can also rotate. When extender sleeve 50 is in a desired position, a sleeve locking mechanisms can securely couple sleeve 50 to inhibit translational and rotational movement of sleeve 50 relative to sleeve collar 40. One example of a mechanism for inhibiting movement of sleeve collar relative to sleeve 50 is sleeve collar set screw 46. By advancing sleeve collar set screw 46 into threads on sleeve collar 40, sleeve collar set screw 46 may contact sleeve 50. Additional advancement of sleeve collar set screw 46 in sleeve collar 40 may bias sleeve collar 40 against sleeve 50 to generate a friction force large enough to inhibit movement of sleeve 50 relative to sleeve collar 40. In other embodiments, a screw can engage a hole in sleeve 50 to prevent translation, a ball or pin can engage a corresponding hole/detent to prevent movement, sleeve collar 40 can be tightened to hold sleeve 50 or other mechanism used to prevent translation and/or rotation of sleeve 50 relative to sleeve collar 40.

Sleeve 50 may couple to bone anchor 60 such that bone anchors 60 can be manipulated using sleeve 50. Sleeve 50 may be coupled to bone anchor 60 before insertion of bone anchor 60 into the patient or may be coupled after bone anchor 60 has been advanced into a vertebra. Sleeve 50 can be used to guide tools and components of a spinal stabilization to the bone anchor 60 for installation of the spinal stabilization system. While only one sleeve is shown in FIG. 1, multiple sleeves 50 can be coupled to support body 10. The sleeves 50 or other components can be manipulated as individuals or as a group.

As can be understood from the foregoing, sleeve 50 can be coupled to support body 10 so that sleeve 50 can be placed in an appropriate longitudinal and lateral position. Additionally, sleeve 50 can rotate about first axis (e.g., parallel to the longitudinal axis), a second axis (perpendicular to the longitudinal axis) and/or polyaxially to position sleeve 50 in a desired orientation relative to the anteriorposterior axis of the patient. This allows a surgeon to place sleeve 50 in a desired longitudinal and lateral position and orientation for a procedure and lock sleeve 50 in that position so that the surgeon's hands are free to manipulate other tools. In some cases the surgeon can unlock one or more degrees of movement of sleeve 50 so that the surgeon can manipulate sleeve 50 in a desired manner during a procedure while preventing movement in undesired directions.

Support body 10 can be helpful in spinal stabilization procedures that involve manipulating the vertebrae. One example of a spinal procedure in which a surgical instrument support may be helpful is in the treatment of a burst fracture. During repair of a burst fracture, the spine must be brought into proper alignment. This may involve multiple steps, such as the following: a first step in which adjacent vertebrae are rotated to correct for an abnormal spine curvature, a second step in which the affected vertebra is distracted, and a third step in which adjacent vertebrae are moved closer to the injured vertebra. Support body 10 provides a stable platform outside of the patient's body for manipulating extender sleeves 50 during such a procedure.

Figure 2A:
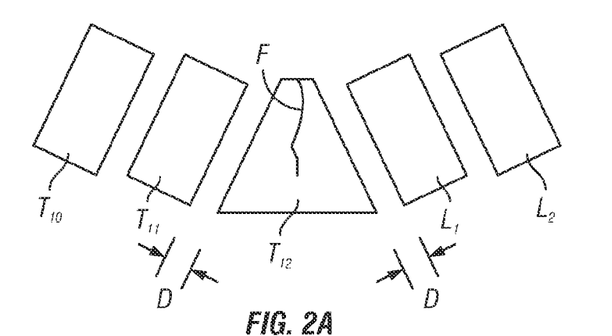
FIG. 2A depicts a side view of a portion of a spine, showing one type of burst fracture.

FIGS. 2A-2D depict a portion of the spine undergoing correction for a burst fracture to vertebra T12. FIGS. 2A-2D are discussed in conjunction with FIG. 1. FIG. 2A depicts a portion of the spine exhibiting an abnormal spine curvature because of a burst fracture. The distance D between the affected vertebra T12 and adjacent vertebrae T11 and L1 may or may not be affected. Fluoroscopic imaging or other medical imaging technique can be used to verify the position or angle of a vertebra, the separation or relative positioning between two or more vertebra and the like.

Figure 2B:
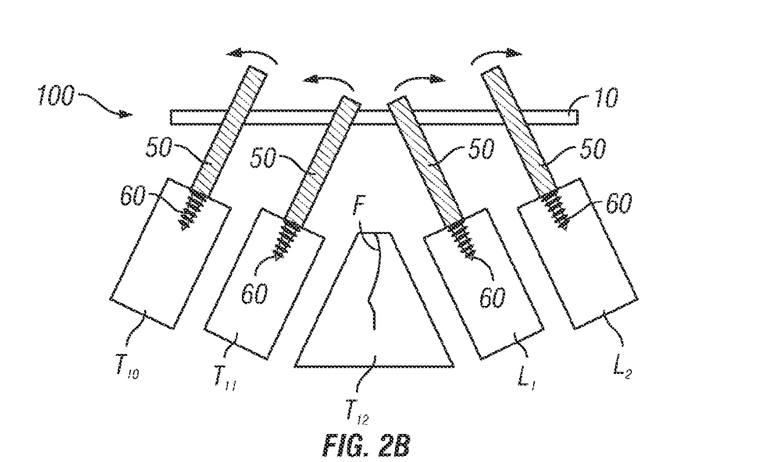
FIG. 2B depicts a side view of a portion of a spine coupled with a portion of one embodiment of a system for manipulating the spine.

Once the injured vertebra has been identified, bone anchors can be placed in one or more vertebrae on either side of the fractured vertebra, such as T10-T11 and L1-L2 for this example. The bone anchors can be installed according to methods known or developed in the art. FIG. 2B depicts a side view of a portion of the spine with bone anchors 60 installed in the adjacent vertebra T10-T11 and L1-L2. Bone anchors 60 are installed using extender sleeves 50. Bone anchors 60 and extender sleeves 50 may be advanced into the patient using minimally-invasive surgery (MIS) procedures or other procedures. As shown in the example of FIG. 2B, multiple sleeves 50 can be inserted in the patient's body at the same time. A parallel row of sleeves may also be used so that there are two (or more) bone anchors are installed in each vertebra.

Support body 10 can be used to position and orient sleeves 50 during installation of anchors 60. Images of the vertebra can be used to determine the correct position and angle of sleeves 50 relative to the patient's body. The surgeon can lock each sleeve 50 in a desired orientation and lateral/longitudinal position while allowing sleeve 50 to translate in sleeve collar 40 to account for the fact that the depth of sleeve 50 changes as it advances into the body. When a bone anchor 60 is in position, the surgeon can optionally lock all motion of the sleeve 50 relative to support instrument support 10.

To correct the curvature of the spine, the extender sleeves 50 on either side of the burst fracture can be rotated away from each other as indicated by the arrows. By way of example, the extender sleeves corresponding to vertebrae L1 and L2 can be rotated in a clockwise direction, while the extender sleeves corresponding to vertebrae T10 and T11 can be rotated in a counter clockwise direction. As each extender sleeve rotates it will move relative to support instrument support 10 in several ways. First, a portion of the sleeve will translate in a longitudinal direction relative to support body 10. Second, the angle of each sleeve 50 will change. Third, the amount each sleeve extends beyond its respective sleeve collar 40 may change. In order to allow for such movement, the surgeon can configure system 100 to allow select degrees of motion for sleeves 50. For example, the surgeon can unlock support body collars 20 associated with vertebrae T10-T11 and L1-L2 so that the support body collars can translate along support instrument support 10, unlock the sleeves 50 so that they can translate in their sleeve collars, and unlock rotation of sleeve collars 40 relative to linkages 30 and/or linkages 30 relative to support body collars 20 to allow the orientation of sleeves 50 to change.

Figure 2C:
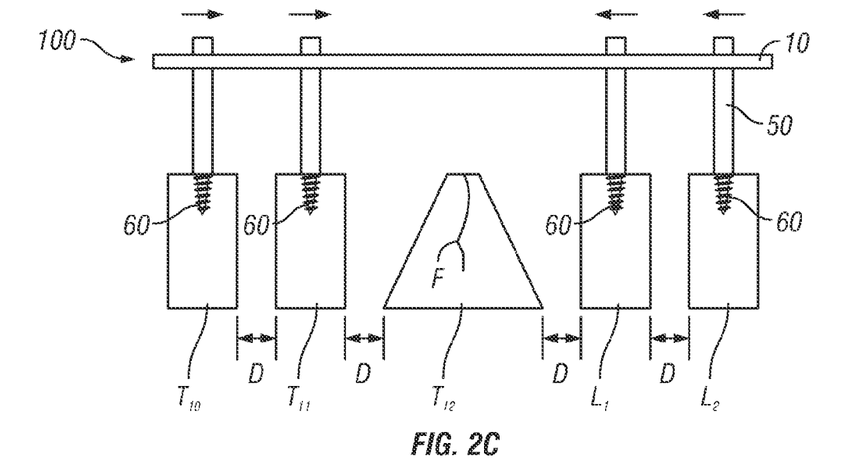
FIG. 2C depicts a side view of a portion of a spine coupled with a portion of one embodiment of a system for manipulating the spine, showing one method for distracting a portion of the spine.

FIG. 2C depicts a view of the spine after the curvature has been corrected. In some cases, it may be desirable to change the distance D between adjacent vertebrae after curvature the curvature of the spine has been corrected. To move vertebrae T10-T11 and L1-L2 closer to T12, support body collars 20 can be disengaged from support instrument support 10 so that they are free to translate while movement and rotation in other directions is inhibited. Support body collars 20 may then be translated along support instrument support 10 in a desired direction (e.g., as indicated by the arrows). Markings 11 on support instrument support 10 can provide an indication of the distance support body collars 20 are to be moved. Once vertebrae T10-T11 and L1-L2 are positioned relative to T12, support body collars 20 may be locked to prevent additional translation.

Figure 2D:
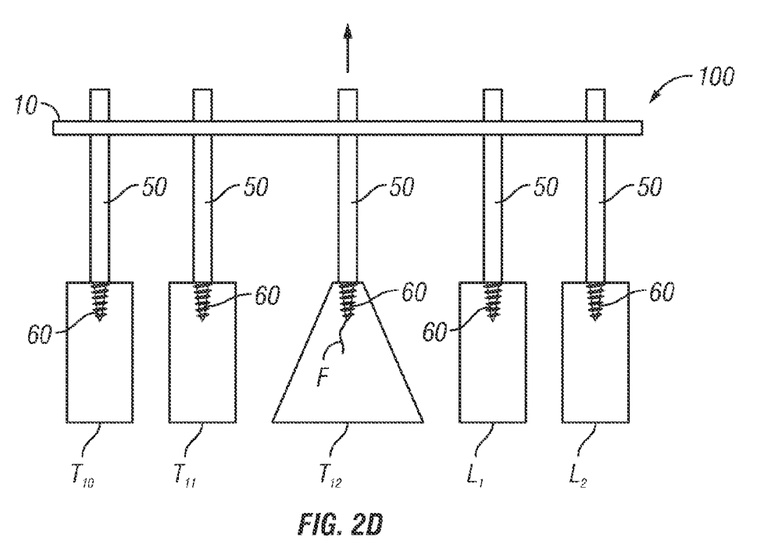
FIG. 2D depicts a side view of a portion of a spine coupled with a portion of one embodiment of a system for manipulating the spine, showing one method for translating a portion of the spine.

FIG. 2D depicts a view of the spine showing distraction of vertebra T12. A bone anchor 60 can be implanted in vertebrae T12 with an extender sleeve 50 coupled to it. The orientation and longitudinal/lateral position of the extender sleeve can be locked to prevent undesired movement. However, extender sleeve 50 can be free to translate in the corresponding sleeve collar 40 so that the surgeon can pull extender sleeve 50 to move vertebrae T12. When vertebrae T12 is in a desired position, the position of extender sleeve 50 relative to sleeve collar 40 can be locked.

Figure 2E:
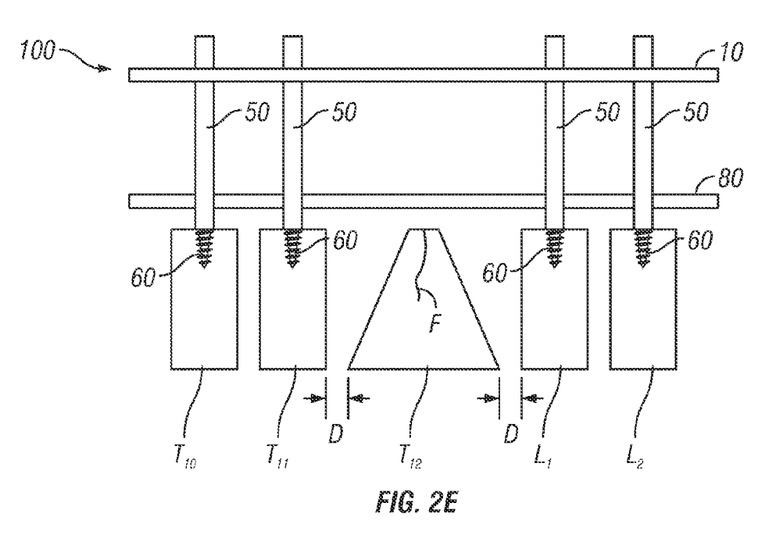
FIG. 2E depicts a view of the spine after angulation and translation of vertebrae in the spine.

FIG. 2E depicts a view of the spine after angulation and translation of vertebrae in the spine. Rod 80 may be inserted in bone screws 60 to lock the spine in place. In some cases, the spinal stabilization rod 80 can also be coupled to vertebra T12. Spinal stabilization rod 80 can be a rigid stabilization rod or can be a dynamic stabilization rod having portions with various degrees of flexibility. Spinal stabilization rod 80 can be installed using any suitable procedure known or developed in the art.

In addition to use in treatment of burst fractures, surgical instrument support 10 can be used in any number of procedures in which extender sleeves are used. Multiple surgical instrument supports may be used as needed or desired. Components of system 100 can be formed any suitable material(s) including, but not limited to, titanium, titanium alloys, stainless steel, ceramics, and/or polymers. Some components of a spinal stabilization system may be autoclaved and/or chemically sterilized. Components that may not be autoclaved and/or chemically sterilized may be made of sterile materials. Components made of sterile materials may be placed in working relation to other sterile components.

Figure 3:
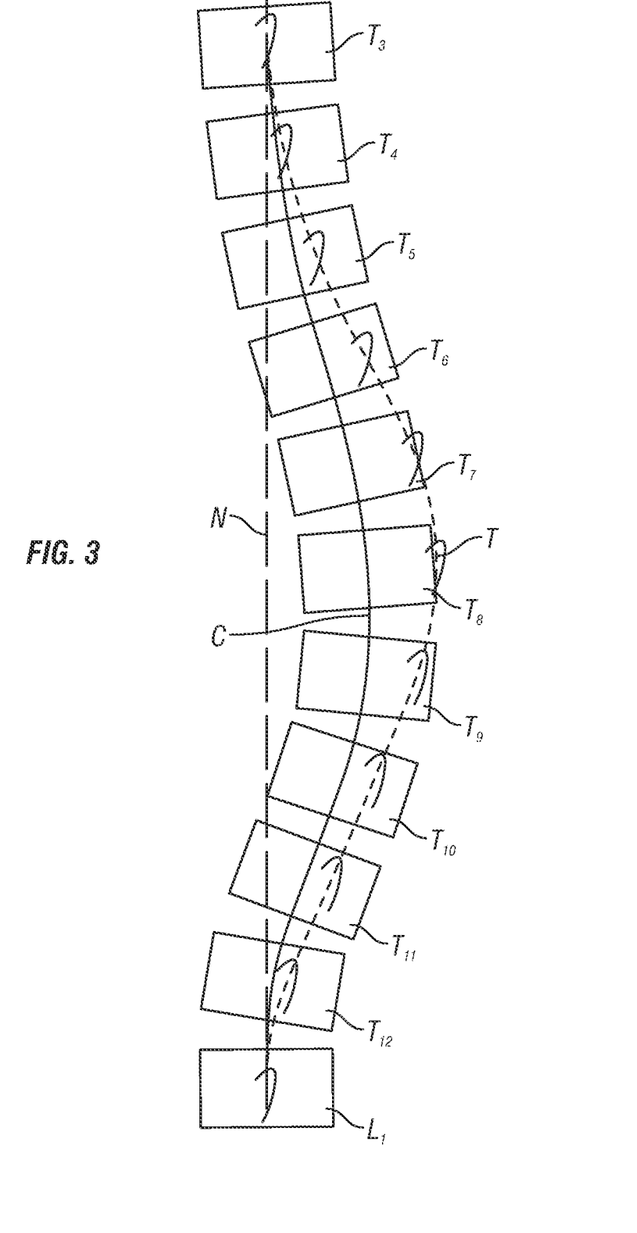
FIG. 3 depicts a posterior view of a portion of the spine, showing one type of abnormal spine curvature.

FIG. 3 depicts a posterior view of a portion of a spine, showing an abnormal curvature such as scoliosis. As depicted in FIG. 3, a spine may have an associated curvature C away from a desired alignment N, and may also be twisted such that the spinous processes have an additional element T. In this type of situation, support body 10 can be used to aid in adjusting vertebrae individually or in groups to correct the curvature. For example, in some embodiments, vertebra T8 may be individually rotated into alignment with vertebrae T7 and T9, vertebrae T7-T9 may be rotated as a group into alignment with vertebrae T6 and T10, and so forth. In some embodiments, vertebra T4-T12 may be rotated as a group until vertebrae T4 and T12 are in alignment with vertebrae T3 and L1, vertebrae T5-T11 may be further rotated until vertebrae T5 and T11 are in alignment with T4 and T12, and so forth. In some embodiments, a first surgical instrument support is used in adjusting vertebrae T3-T8 and a second surgical instrument support is used in adjusting vertebrae T9-L1. An advantage to translating and rotating vertebrae as a group may be the distribution of forces, which may reduce the likelihood of injuring the patient during surgery.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system for positioning components in surgical procedures comprising;
   a surgical instrument support having a support body comprising a first member and second member having parallel portions extending in a first direction;
   a support body collar mounted to the first member and translatable along the first member;
   a support body collar locking mechanism to selectively inhibit translation of the support body collar;
   a linkage coupled to the support body collar translatable relative to the support body collar perpendicular to the first direction;
   a linkage locking mechanism to selectively inhibit translation of the linkage relative to the support body collar;
   a crossbar coupled to the support body collar and extending between the first member and the second member;
   a sleeve collar coupled to the linkage by a connection that allows polyaxial rotation of the sleeve collar relative to the linkage, wherein the sleeve collar is sized to receive an extender sleeve for installing bone anchors and allow the extender sleeve to translate in the sleeve collar;
   a sleeve collar locking mechanism to inhibit rotation of the sleeve collar;
   an extender sleeve locking mechanism to inhibit translation of the extender sleeve in the sleeve collar.

2. The system of claim 1, further comprising:
   a bone anchor;
   an extender sleeve passing through the sleeve collar and coupled to the bone anchor.

3. The system of claim 2, wherein the sleeve collar has an opening having a complementary shape to an outside shape of the extender sleeve.

4. The system of claim 1, wherein the first member is slidably connected to the second member and wherein the system further comprises a set of connectors for securely joining the first and second members.

5. The system of claim 1, wherein the support body has a curvature based on a desired curvature of a portion of the spine.

6. The system of claim 1, wherein the support body comprises a set of markings.

7. The system of claim 1, wherein the support body forms a substantially rectangular shape.

8. The system of claim 1, wherein the support body collar locking mechanism comprises a support body collar set screw and wherein advancing the support body collar set screw in the support body collar biases the support body collar against the support body to inhibit movement of the support body collar relative to the frame.

9. The system of claim 1, wherein the linkage is rotatable relative to the support body collar about an axis of rotation perpendicular to the first direction and wherein the linkage locking mechanism is adapted to selectively inhibit rotation of the linkage relative to the support body collar.

10. The system of claim 9, wherein the linkage locking mechanism comprises a linkage set screw and wherein advancing the linkage set screw in the support body collar biases the linkage against the support body collar to inhibit movement of the linkage relative to the support body collar.

11. The system of claim 1, wherein the sleeve locking mechanism comprises a sleeve set screw and wherein advancing the sleeve set screw biases the sleeve against the sleeve collar to inhibit translation of the sleeve in the sleeve collar.

12. The system of claim 1, wherein the sleeve collar is coupled to the linkage by a ball and socket joint.

13. The system of claim 12, wherein the support body collar locking mechanism comprises a support body collar set screw and wherein advancing the support body collar set screw biases the ball against a surface of the socket to inhibit rotation of the support body collar.

14. A system for positioning components in surgical procedures comprising;
   a surgical instrument support having a support body comprising a first member and second member having parallel portions extending in a first direction, the first member slidably connected to the second member and wherein the system further comprises a set of connectors for securely joining the first and second members;
   a support body collar mounted to the first member and translatable along the first member;

a support body collar locking mechanism to selectively inhibit translation of the support body collar;

a linkage coupled to the support body collar translatable relative to the support body collar perpendicular to the first direction;

a linkage locking mechanism to selectively inhibit translation of the linkage relative to the support body collar;

a sleeve collar coupled to the linkage by a connection that allows polyaxial rotation of the sleeve collar relative to the linkage, wherein the sleeve collar is sized to receive an extender sleeve for installing bone anchors and allow the extender sleeve to translate in the sleeve collar;

a sleeve collar locking mechanism to inhibit rotation of the sleeve collar;

an extender sleeve locking mechanism to inhibit translation of the extender sleeve in the sleeve collar.

15. The system of claim 14, further comprising:

a bone anchor;

an extender sleeve passing through the sleeve collar and coupled to the bone anchor.

16. The system of claim 15, wherein the linkage is rotatable relative to the support body collar about an axis of rotation perpendicular to the first direction and wherein the linkage locking mechanism is adapted to selectively inhibit rotation of the linkage relative to the support body collar.

17. The system of claim 14, wherein the support body collar locking mechanism comprises a support body collar set screw and wherein advancing the support body collar set screw in the support body collar biases the support body collar against the support body to inhibit movement of the support body collar relative to the frame.

18. A system for positioning components in surgical procedures comprising;

a surgical instrument support having a support body comprising a first member and second member having parallel portions extending in a first direction;

a support body collar mounted to the first member and translatable along the first member;

a support body collar locking mechanism to selectively inhibit translation of the support body collar;

a linkage coupled to the support body collar translatable relative to the support body collar perpendicular to the first direction;

a linkage locking mechanism to selectively inhibit translation of the linkage relative to the support body collar;

a sleeve collar coupled to the linkage by a connection that allows polyaxial rotation of the sleeve collar relative to the linkage, wherein the sleeve collar is sized to receive an extender sleeve for installing bone anchors and allow the extender sleeve to translate in the sleeve collar;

a sleeve collar locking mechanism, the sleeve locking mechanism comprising a sleeve set screw and wherein advancing the sleeve set screw biases the sleeve against the sleeve collar to inhibit translation of the sleeve in the sleeve collar;

an extender sleeve locking mechanism to inhibit translation of the extender sleeve in the sleeve collar.

19. The system of claim 18, further comprising:

a bone anchor;

an extender sleeve passing through the sleeve collar and coupled to the bone anchor.

20. The system of claim 18, wherein the sleeve collar is coupled to the linkage by a ball and socket joint.

21. The system of claim 20, wherein the support body collar locking mechanism comprises a support body collar set screw and wherein advancing the support body collar set screw biases the ball against a surface of the socket to inhibit rotation of the support body collar.

* * * * *